(12) United States Patent
Yu

(10) Patent No.: US 10,071,391 B2
(45) Date of Patent: Sep. 11, 2018

(54) ATOMIZING SPRAYER

(71) Applicant: QUATEK HOLDING INC., Taipei (TW)

(72) Inventor: Neng-Chih Yu, Taipei County (TW)

(73) Assignee: QUATEK HOLDING INC., Taipei (TW)

( * ) Notice: Subject to any disclaimer, the term of this patent is extended or adjusted under 35 U.S.C. 154(b) by 885 days.

(21) Appl. No.: 14/618,146

(22) Filed: Feb. 10, 2015

(65) Prior Publication Data

US 2015/0231660 A1 Aug. 20, 2015

(30) Foreign Application Priority Data

Feb. 14, 2014 (TW) .............................. 103104911 A

(51) Int. Cl.
| | | |
|---|---|---|
| *A61M 11/00* | (2006.01) | |
| *B05B 17/00* | (2006.01) | |
| *A45D 34/00* | (2006.01) | |
| *A45D 34/02* | (2006.01) | |

(52) U.S. Cl.
CPC .......... *B05B 17/0646* (2013.01); *A45D 34/00* (2013.01); *A45D 34/02* (2013.01); *A61M 11/005* (2013.01); *A45D 2200/057* (2013.01)

(58) Field of Classification Search
CPC . B05B 17/06; B05B 17/0607; B05B 17/0638; B05B 17/0646; A61M 11/005
See application file for complete search history.

(56) References Cited

U.S. PATENT DOCUMENTS

| | | | | |
|---|---|---|---|---|
| 4,550,325 A | * | 10/1985 | Viola | ................... B41J 2/14298 222/202 |
| 8,638,023 B2 | * | 1/2014 | Liu | ..................... B05B 17/0646 310/323.01 |
| 8,925,833 B2 | * | 1/2015 | Ki | ......................... A45D 34/04 239/102.1 |
| 9,289,792 B2 | * | 3/2016 | Hogan | ................ B05B 17/0646 |
| 2006/0086819 A1 | * | 4/2006 | Litherland | ........... A61M 11/005 239/102.1 |
| 2006/0243820 A1 | * | 11/2006 | Ng | ...................... B05B 17/0646 239/102.1 |
| 2011/0011396 A1 | * | 1/2011 | Fang | ..................... A24F 47/008 128/202.21 |
| 2012/0012665 A1 | * | 1/2012 | Ivri | ...................... A61M 11/005 239/4 |

(Continued)

*Primary Examiner* — LaToya M Louis
(74) *Attorney, Agent, or Firm* — WPAT, PC

(57) ABSTRACT

An atomizing sprayer includes a vapor tube, a front washer, an ultrasonic chip, a porous plate holder, a porous plate, a rear washer, and a chip holder. The chip holder has an opening hole at its center. One side of the chip holder has an accommodating space and a circular groove. The rear washer is disposed in the circular groove and its outer surface leans against the edge of the central hole of the ultrasonic chip. The porous plate holder is disposed on the ultrasonic chip and the porous plate is disposed on the porous plate holder. The outer protrusion ring of the front washer leans against the porous plate holder and the inner protrusion ring of the front washer leans against the porous plate, so the assembly of the ultrasonic chip, the porous plate holder and the porous plate can be fixed between the front and rear washers.

16 Claims, 6 Drawing Sheets

(56) References Cited

U.S. PATENT DOCUMENTS

| | | | |
|---|---|---|---|
| 2012/0091224 A1* | 4/2012 | Yu | B05B 17/0646 239/102.2 |
| 2012/0111970 A1* | 5/2012 | Hogan | A61M 15/0085 239/102.2 |
| 2012/0234321 A1* | 9/2012 | Power | A61B 17/3474 128/203.12 |
| 2013/0074832 A1* | 3/2013 | Gallem | A61M 11/005 128/200.14 |
| 2013/0245380 A1* | 9/2013 | Vogel | A61B 1/32 600/205 |

* cited by examiner

ATOMIZING SPRAYER

CROSS-REFERENCE TO RELATED APPLICATION

This application claims the benefit of Taiwan Patent Application No. 103104911, filed on Feb. 14, 2014, in the Taiwan Intellectual Property Office, the disclosure of which is incorporated herein in its entirety by reference.

BACKGROUND OF THE INVENTION

1. Field of the Invention

The present invention generally relates to an atomizing sprayer structure, in particular to a high-performance atomizing sprayer structure applicable to the medical purpose or beauty purpose; the structure design of the atomizing porous plate of the atomizing sprayer structure is of more safety, which can effectively prevent the component of the atomizing sprayer from dropping off and then being accidentally aspirated by the user.

2. Description of the Related Art

In general, the atomizing effect of most atomizers is achieved by using a porous plate and the ultrasonic principle to transmit energy to the porous plate by the resonant effect of the ultrasonic transducer and then generate the atomizing effect via the surface acoustic effect.

The conventional micro atomizers can be comprehensively applied to the medical purpose or beauty purpose; users may use a micro atomizer to perform inhalation drug therapy or beauty application. Compared with oral medicine, the atomizer can atomize liquid medicine into extremely fine mist; therefore, it is vary effective for patients with bronchiectasis or lung disease. Besides, the micro atomizer is very light, so it is very easy to carry about, which is very convenient for user.

How fast an atomizer atomizes liquid medicine stands for the performance of the atomizer. The conventional atomizers have been improved to be of small size, low power consumption and high atomizing rate; however, now people pay more attention to the safety of the conventional atomizers.

Please refer to FIG. 1, which is the explosion diagram of the atomizing sprayer of a conventional atomizer. As shown in FIG. 1, the atomizing sprayer includes a casing 100, two washers 200, a piezoelectric plate 300, a plate holder 310, a nozzle plate 320 and a base 400. Please further refer to FIG. 2, which is the cross-section diagram of the conventional atomizer. As shown in FIG. 2, the plate holder 310 is attached to the piezoelectric plate 300 by gel; similarly, the nozzle plate 320 is also attached to the plate holder 310 by gel. The two washers 200 are respectively disposed on the front side and the rear side of the assembly of the piezoelectric plate 300, the plate holder 310 and the nozzle plate 320. The casing 100 has a groove for accommodating one of the washers 200; the base 400 also has a groove for accommodating the other one of the washers 200. The casing 100 can be engaged with the base 400 to fix the assembly of the piezoelectric plate 300, the plate holder 310 and the nozzle plate 320. As shown in FIG. 2, the piezoelectric plate 300 of the ultrasonic transducer will generate ultrasonic vibration and transmit which to the nozzle plate 320 to vibrate it; then the liquid 510 in the tank 500 will be sprayed from the nozzle plate 320 to generate atomized liquid 110. However, as the structure of the atomizing sprayer of the conventional atomizer cannot firmly fix the nozzle plate 320, the nozzle plate 320 may drop off from the plate holder 310 and then fall out of the opening of the casing 100; therefore, when using the atomizer, the user may aspirate the nozzle plate 320 into his body by accident, which may seriously damage the user.

As described above, for the purpose of preventing the components of an atomizer from dropping off and being accidentally aspirated by users, the inventor of the invention keeps trying hard to improve the structure of the conventional atomizer in order to solve the critical problem of the conventional atomizer and provide a better and safer atomizer.

SUMMARY OF THE INVENTION

To achieve the foregoing objective, the present invention provides an atomizer, in particular to the structure of the atomizing sprayer of the atomizer The atomizing sprayer may include a vapor tube, a front washer, an ultrasonic chip, a porous plate holder, a porous plate, a rear washer, and a chip holder. The chip holder may have an opening hole at its center. One side of the chip holder may have an accommodating space and a circular groove, wherein the rear washer may be disposed in the circular groove and its outer surface leans against the edge of the central hole of the ultrasonic chip. The porous plate holder may be disposed on the ultrasonic chip and the porous plate is disposed on the porous plate holder.

The outer protrusion ring of the front washer may lean against the porous plate holder and the inner protrusion ring of the front washer may lean against the porous plate, so the assembly of the ultrasonic chip, the porous plate holder and the porous plate can be firmly fixed between the front and the rear washers.

The porous plate of the atomizing sprayer according to the invention is to generate ultrasonic vibration via the ultrasonic chip inside the sprayer to vibrate the porous plate and then atomize the liquid medicine in the tank of the atomizer via the porous plate; then, the atomized liquid medicine will be sprayed from the vapor tube. The invention is characterized in that the assembly of the ultrasonic chip, the porous plate holder and the porous plate may be firmly fixed by the outer protrusion ring of the front washer and the protrusion ring of the rear washer; the inner protrusion ring of the front washer may lean against the porous plate, and the inner diameter of the inner protrusion ring is smaller than the outer diameter of the porous plate so as to prevent the porous plate from dropping off.

To achieve the foregoing objective, the present invention provides an atomizer, in particular to the structure of the atomizing sprayer of the atomizer The atomizing sprayer may include a vapor tube, a front washer, an ultrasonic chip, a porous plate holder, a porous plate, a rear washer, and a chip holder. The chip holder may have an opening hole at its center. One side of the chip holder may have an accommodating space and a circular groove, wherein the rear washer may be disposed in the circular groove and its outer surface leans against the edge of the central hole of the ultrasonic chip. The porous plate holder may be disposed on the ultrasonic chip and the porous plate disposed on the porous plate holder. The outer protrusion ring of the front washer may lean against the porous plate holder and the inner protrusion ring of the front washer may lean against the porous plate, so the assembly of the ultrasonic chip, the porous plate holder and the porous plate can be firmly fixed between the front and the rear washers. The inner diameter of the spray hole of the vapor tube is smaller than the outer diameter of the porous plate.

The invention is characterized in that the inner diameter of the spray hole of the vapor tube is smaller than the outer diameter of the porous plate, which can effectively prevent the porous plate from falling out of the vapor tube to enhance the safety of the atomizer

BRIEF DESCRIPTION OF THE DRAWINGS

The detailed structure, operating principle and effects of the present invention will now be described in more details hereinafter with reference to the accompanying drawings that show various embodiments of the invention as follows.

DETAILED DESCRIPTION OF THE PREFERRED EMBODIMENTS

The technical content of the present invention will become apparent by the detailed description of the following embodiments and the illustration of related drawings as follows.

Figure 1:
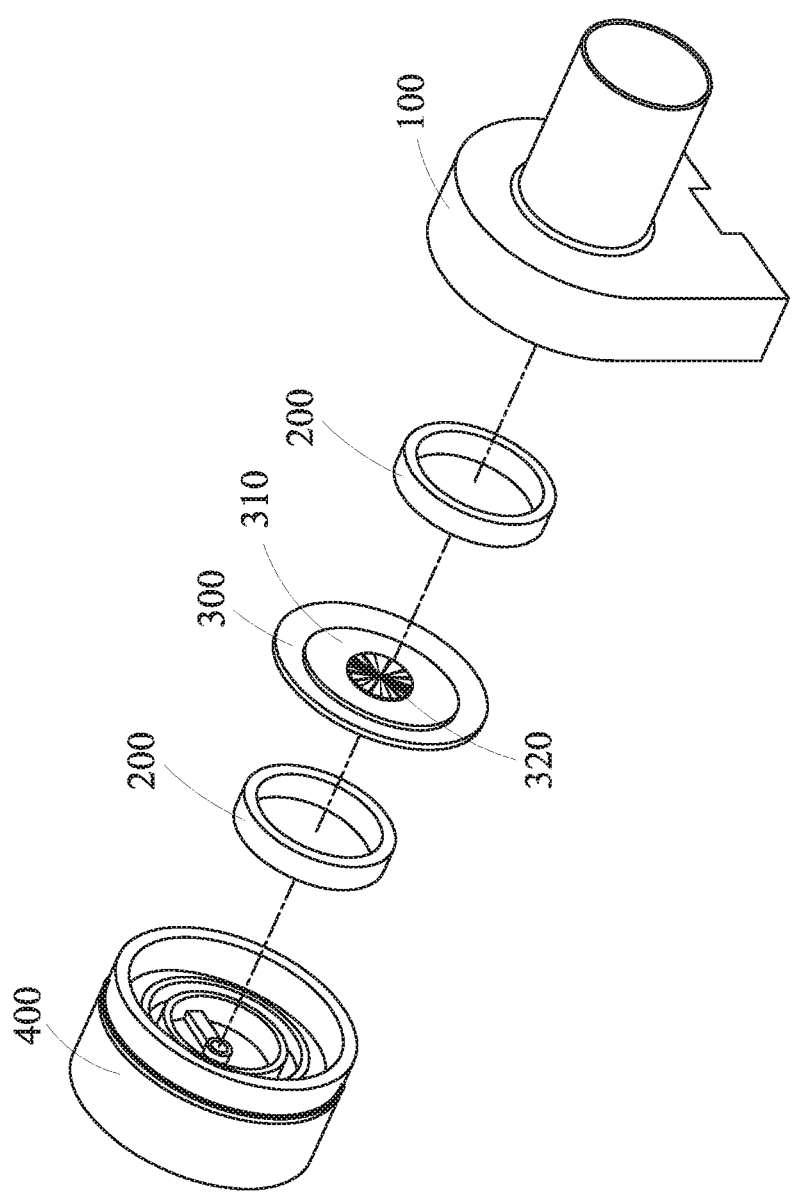
FIG. 1 is the explosion diagram of the atomizing sprayer of a conventional atomizer.
Figure 2:
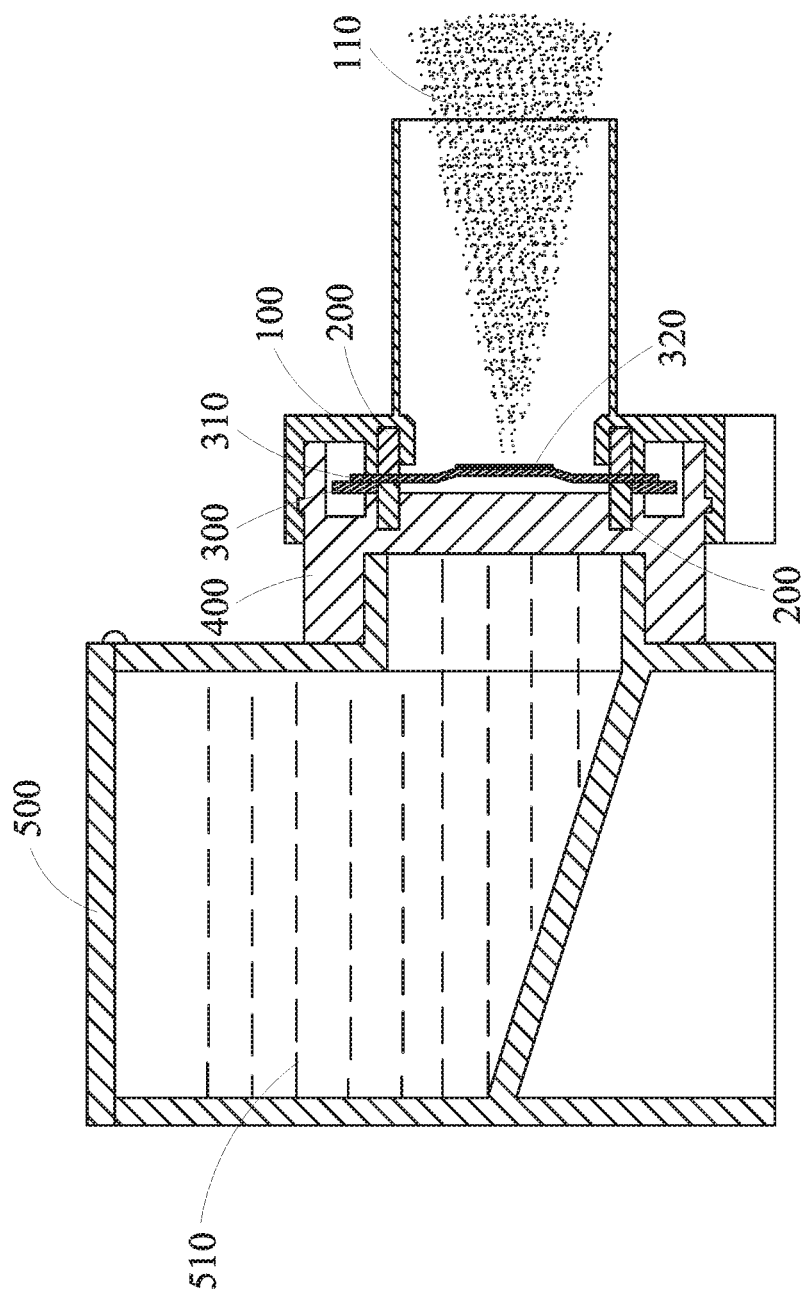
FIG. 2 is the cross-section diagram of the conventional atomizer.
Figure 3:
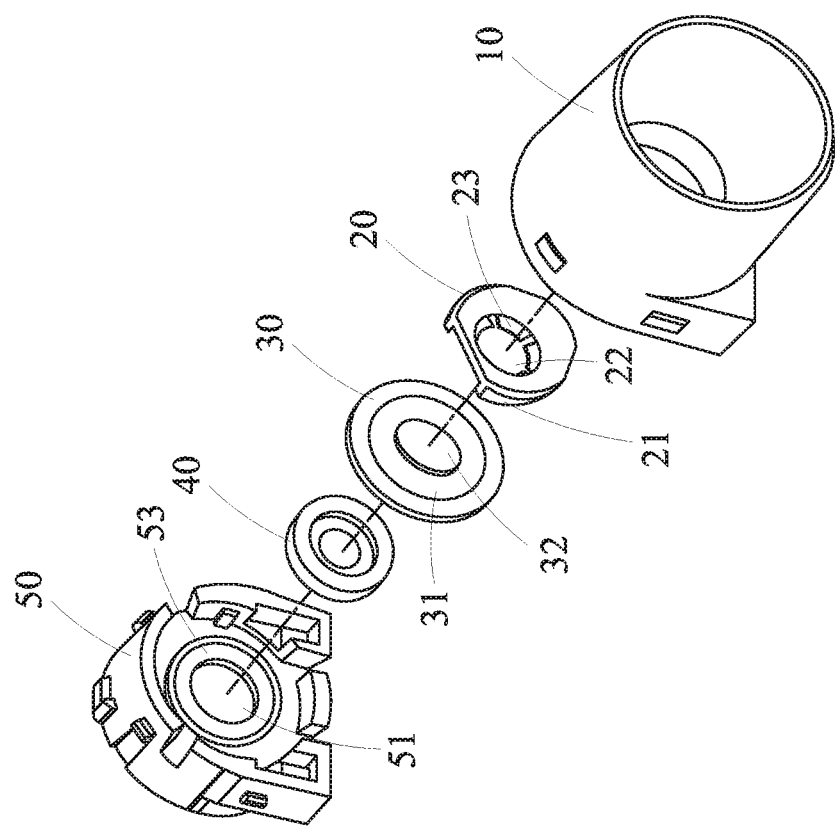
FIG. 3 is the explosion diagram of the atomizing sprayer of the first embodiment in accordance with the invention.
Figure 4:
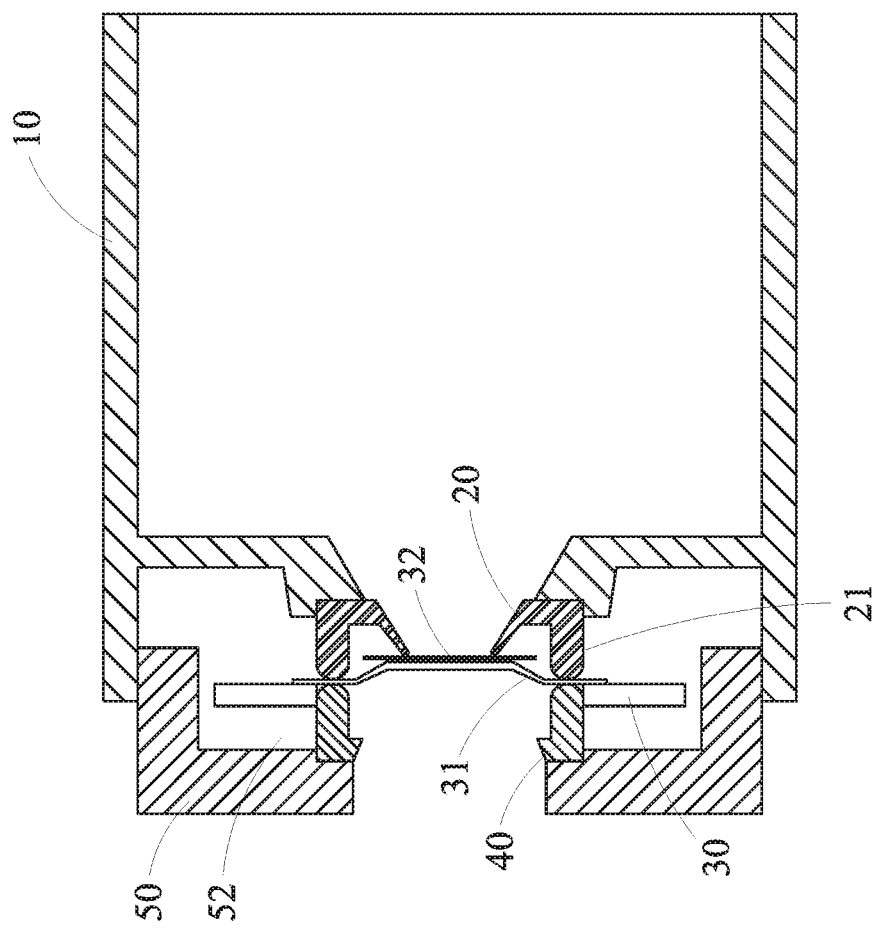
FIG. 4 is the cross-section diagram of the atomizing sprayer of the first embodiment in accordance with the invention.

Please refer to FIG. 3 and FIG. 4; FIG. 3 is the explosion diagram of the atomizing sprayer of the first embodiment in accordance with the invention, and FIG. 4 is the cross-section diagram of the atomizing sprayer of the first embodiment in accordance with the invention. In the embodiment, the atomizing sprayer may include a vapor tube 10, a front washer 20, an ultrasonic chip 30, a porous plate holder 31, a porous plate 32, a rear washer 40, and a chip holder 50. One side of the chip holder 50 may have an accommodating space 52 and a circular groove 53, wherein the rear washer 40 may be disposed in the circular groove 53 and the outer surface of the rear washer 40 may lean against the edge of the central hole of the ultrasonic chip 30. The porous plate holder 31 may be disposed on the ultrasonic chip 30 and the porous plate 32 may be disposed on the porous plate holder 31. The assembly of the ultrasonic chip 30, the porous plate holder 31 and the porous plate 32 may be fixed between the front washer 20 and the rear washer 40 by the outer protrusion ring 21 of the front washer 20. Finally, the vapor tube 10 is engaged with the chip holder 50 to form the atomizing sprayer of the embodiment. In the embodiment, the porous plate 32 may be made of plastics or metal; the front washer 20 and the rear washer 40 may be made of silicon gel; the porous plate holder 31 may be made of metal.

In the embodiment, the ultrasonic chip, the porous plate holder and the porous plate may be connected to one another by glue in order to quickly and conveniently connect them to one another.

As shown in FIG. 4, the porous plate 31 may drop off from the porous plate holder 31 and then fall out of the vapor tube 10; thus, for the purpose of improving the shortcoming, the front washer 20 in the embodiment may further include an inner protrusion ring 22 and the inner protrusion ring 22 may diagonally extend from the front washer 20. The inner protrusion ring 22 and the outer protrusion ring 21 are at the same side of the front washer 20 and may respectively lean against the porous plate 32 and the porous plate holder 31 so as to prevent the vapor tube 10 from dropping out of the vapor tube 10 and being accidentally aspirated by the user.

Moreover, the inner protrusion ring 22 of the front washer 20 may further include a plurality of protruding claws 23. As the front washer 20 may be made of flexible material, such as silicone gel, the front washer 20 with above structure can provide proper force to support the porous plate 32.

Figure 5:
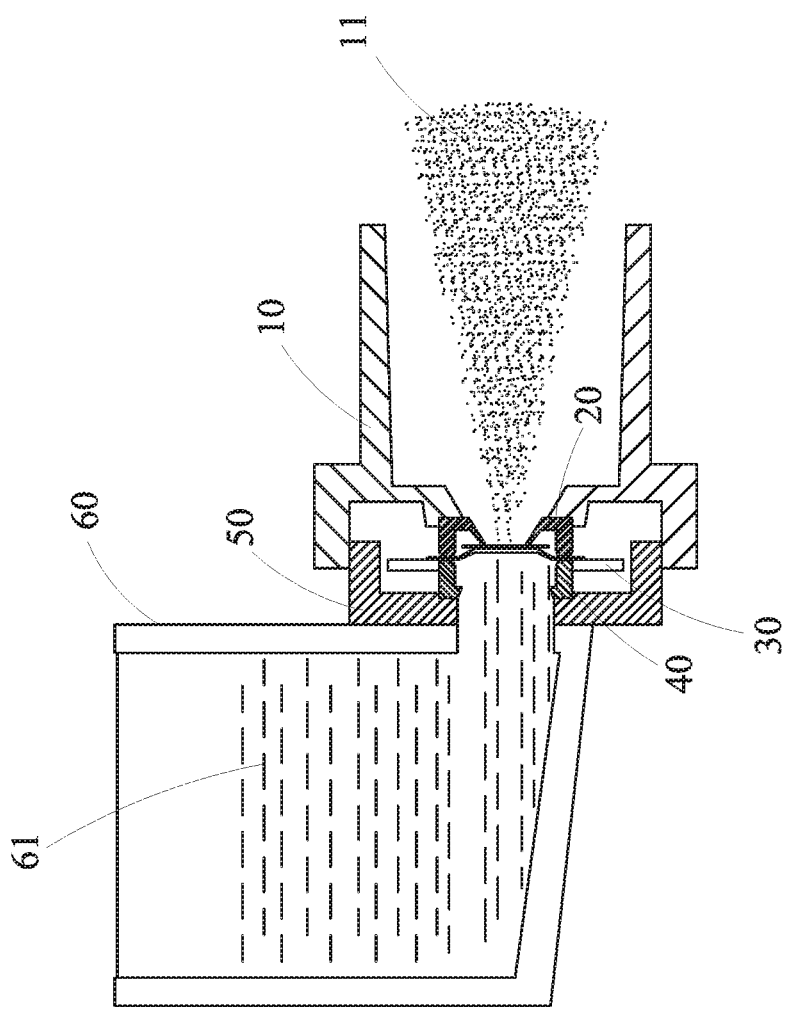
FIG. 5, which is the schematic view of the atomizing sprayer of the first embodiment in accordance with the invention.

Please refer to FIG. 5, which is the schematic view of the atomizing sprayer of the first embodiment in accordance with the invention, which illustrates the usage situation that the atomizing sprayer is spraying liquid medicine 61 in the tank of the atomizer As shown in FIG. 5, the ultrasonic chip 30 will generate ultrasonic vibration to vibrate the porous plate 32; then, the liquid medicine 61 is atomized by the porous plate 32 and then the atomized liquid medicine 11 is sprayed from the porous plate 32.

Figure 6:
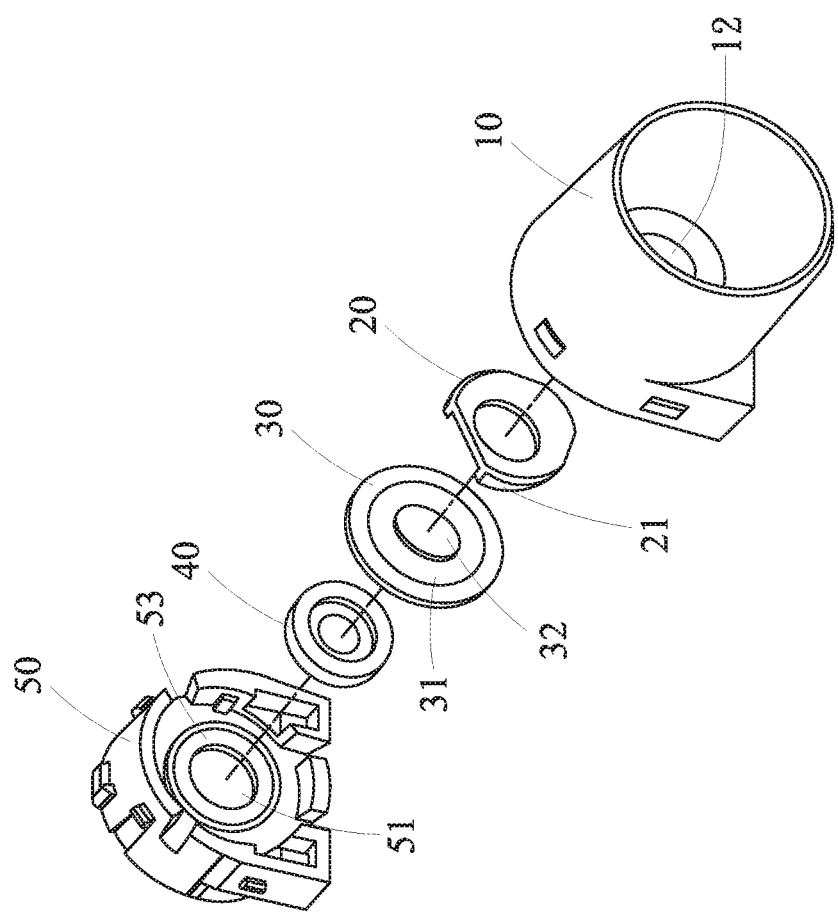
FIG. 6, which is the explosion diagram of the atomizing sprayer of the second embodiment in accordance with the invention.

Please refer to FIG. 6, which is the explosion diagram of the atomizing sprayer of the second embodiment in accordance with the invention. In the embodiment, the atomizing sprayer may include a vapor tube 10, a front washer 20, an ultrasonic chip 30, a porous plate holder 31, a porous plate 32, a rear washer 40, and a chip holder 50.

In the embodiment, the atomizing sprayer may include a vapor tube 10, a front washer 20, an ultrasonic chip 30, a porous plate holder 31, a porous plate 32, a rear washer 40, and a chip holder 50. One side of the chip holder 50 may have an accommodating space 52 and a circular groove 53, wherein the rear washer 40 may be disposed in the circular groove 53 and the outer surface of the rear washer 40 may lean against the edge of the central hole of the ultrasonic chip 30. The porous plate holder 31 may be disposed on the ultrasonic chip 30 and the porous plate 32 may be disposed on the porous plate holder 31. The assembly of the ultrasonic chip 30, the porous plate holder 31 and the porous plate 32 may be fixed between the front washer 20 and the rear washer 40 by the outer protrusion ring 21 of the front washer 20. The difference between this embodiment and the previous embodiment is that the inner diameter of the spray hole 12 of the vapor tube 10 in this embodiment is smaller than the outer diameter of the porous plate 32, which can also effectively prevent the porous plate 32 from falling out of the vapor tube 10.

To sum up, the first embodiment and the second embodiment of the present invention improve the structure of the atomizing sprayer, which have the following advantages:

1. The porous plate can be firmly fixed by the front washer; besides, the front washer can be made of flexible material, which can provide excellent shock absorbing effect and prevent the porous plate from being damaged.

2. The front washer can be made of non-metal material, such as silicone gel, which can provide excellent insulation effect.

3. Once the porous plate drops off from the porous plate holder, the inner protrusion ring of the front washer or the vapor tube can effectively prevent the porous plate from falling out of the vapor tube and then being accidentally aspirated by the user, which enhances the safety of the atomizer While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. An atomizing sprayer, comprising a vapor tube, a front washer, an ultrasonic chip, a porous plate holder, a porous plate, a rear washer, and a chip holder, wherein there is a an opening hole at a center of the chip holder; one side of the chip holder has an accommodating space and a circular groove, and the rear washer is disposed in the circular groove and an outer surface of the rear washer leans against an edge of a central hole of the ultrasonic chip; the porous plate holder is disposed on the ultrasonic chip and the porous plate is disposed on the porous plate holder; the ultrasonic chip, the porous plate holder and the porous plate are fixed between the front washer and the rear washer by an outer protrusion ring of the front washer; the vapor tube is engaged with the chip holder, wherein the front washer further comprises an inner protrusion ring diagonally extending from the front washer; the inner protrusion ring and the outer protrusion ring are at the same side of the front washer; the inner protrusion ring leans against the porous plate, and the outer protrusion ring leans against the porous plate holder.

2. The atomizing sprayer of claim 1, wherein the ultrasonic chip, the porous plate holder and the porous plate are connected to one another by glue.

3. The atomizing sprayer of claim 1, wherein an inner diameter of the inner protrusion ring of the front washer is smaller than an outer diameter of the porous plate.

4. The atomizing sprayer of claim 3, wherein the inner protrusion ring of the front washer further comprises a plurality of protruding claws.

5. The atomizing sprayer of claim 4, wherein the porous plate is made of metal.

6. The atomizing sprayer of claim 4, wherein the porous plate is made of plastics.

7. The atomizing sprayer of claim 1, wherein the front washer and the rear washer are made of silicone gel.

8. The atomizing sprayer of claim 1, wherein the porous plate holder is made of metal.

9. An atomizing sprayer, comprising a vapor tube, a front washer, an ultrasonic chip, a porous plate holder, a porous plate, a rear washer, and a chip holder, wherein there is a an opening hole at a center of the chip holder; one side of the chip holder has an accommodating space and a circular groove, and the rear washer is disposed in the circular groove and an outer surface of the rear washer leans against an edge of a central hole of the ultrasonic chip; the porous plate holder is disposed on the ultrasonic chip and the porous plate is disposed on the porous plate holder; the ultrasonic chip, the porous plate holder and the porous plate are fixed between the front washer and the rear washer by an outer protrusion ring of the front washer; an inner diameter of the a spray hole of the vapor tube is smaller than an outer diameter of the porous plate, and the vapor tube is engaged with the chip holder, wherein the front washer further comprises an inner protrusion ring diagonally extending from the front washer; the inner protrusion ring and the outer protrusion ring are at the same side of the front washer; the inner protrusion ring leans against the porous plate, and the outer protrusion ring leans against the porous plate holder.

10. The atomizing sprayer of claim 9, wherein the ultrasonic chip, the porous plate holder and the porous plate are connected to one another by glue.

11. The atomizing sprayer of claim 9, wherein an inner diameter of the inner protrusion ring of the front washer is smaller than an outer diameter of the porous plate.

12. The atomizing sprayer of claim 11, wherein the inner protrusion ring of the front washer further comprises a plurality of protruding claws.

13. The atomizing sprayer of claim 12, wherein the porous plate is made of metal.

14. The atomizing sprayer of claim 12, wherein the porous plate is made of plastics.

15. The atomizing sprayer of claim 9, wherein the front washer and the rear washer are made of silicone gel.

16. The atomizing sprayer of claim 9, wherein the porous plate holder is made of metal.

* * * * *